(12) United States Patent
Muldoon et al.

(10) Patent No.: US 9,993,424 B2
(45) Date of Patent: Jun. 12, 2018

(54) INTRAVAGINAL MATRIX DRUG DELIVERY DEVICES

(75) Inventors: Brendan Muldoon, Newtownabbey (GB); Colin Lorimer, Lisburn (GB); Claire Gilligan, Belfast (GB)

(73) Assignee: Allergan Pharmaceuticals International Limited, Dublin (IE)

( * ) Notice: Subject to any disclaimer, the term of this patent is extended or adjusted under 35 U.S.C. 154(b) by 31 days.

(21) Appl. No.: 10/472,901

(22) PCT Filed: Mar. 27, 2003

(86) PCT No.: PCT/EP03/03305
§ 371 (c)(1),
(2), (4) Date: Sep. 25, 2003

(87) PCT Pub. No.: WO03/080018
PCT Pub. Date: Oct. 2, 2003

(65) Prior Publication Data
US 2005/0042292 A1  Feb. 24, 2005

(30) Foreign Application Priority Data
Mar. 27, 2002 (IE) .................................. S2002/0226

(51) Int. Cl.
*A61F 13/02* (2006.01)
*A61K 9/00* (2006.01)

(52) U.S. Cl.
CPC .................................. *A61K 9/0036* (2013.01)

(58) Field of Classification Search
CPC .................................................... A61K 9/0036
USPC .................................................. 424/430, 431
See application file for complete search history.

(56) References Cited

U.S. PATENT DOCUMENTS

| | | | |
|---|---|---|---|
| 3,545,439 A | 12/1970 | Duncan | |
| 3,920,805 A | 11/1975 | Roseman | 424/19 |
| 3,992,518 A | 11/1976 | Chien et al. | 424/22 |
| 4,012,497 A * | 3/1977 | Schopflin | 424/432 |
| 4,155,991 A * | 5/1979 | Schopflin et al. | 424/432 |
| 4,264,577 A | 4/1981 | Zimmerman et al. | 424/22 |
| 4,292,965 A | 10/1981 | Nash et al. | 424/22 |
| 4,888,074 A | 12/1989 | Pocknell | 156/217 |
| 5,188,835 A * | 2/1993 | Lindskog et al. | 424/432 |
| 5,788,980 A | 8/1998 | Nabahi | 424/430 |
| 5,837,313 A | 11/1998 | Ding et al. | |
| 5,855,906 A | 1/1999 | McClay | 422/433 |
| 5,972,372 A | 10/1999 | Saleh et al. | 424/432 |
| 6,063,395 A | 5/2000 | Markkula et al. | 424/422 |
| 6,103,256 A * | 8/2000 | Nabahi | 424/430 |
| 6,126,958 A | 10/2000 | Saleh et al. | 424/432 |

FOREIGN PATENT DOCUMENTS

| | | |
|---|---|---|
| EP | 0 887 074 A2 | 12/1998 |
| WO | 98/50016 | 9/1998 |
| WO | 02/076426 | 10/2002 |
| WO | 02/076426 A2 | 10/2002 |

OTHER PUBLICATIONS

Woolfson A.D. et al. "Design of an intravaginal ring for the controlled delivery of 17β-estradiol as its 3-acetate ester", Journal of Controlled Release 61 (1999) pp. 319-328.
Opposition against European Patent No. 1 494 646, dated Apr. 10, 2013.
Lee, Chi-Hyun, et al., Development of Silicone-Based Barrier Devices for Controlled Delivery of Spermicidal Agents, Journal of Controlled Release 44. pp. 43-53, (1997).
Chien, Y. W., et al., "Controlled Drug Release from Polymeric Delivery Devices V: Hydroxy Group Effects on Drug Release Kinetics and Thermodynamics", Journal of Pharmaceutical Science, vol. 68, No. 6, pp. 689-693, (1978).
Written Decision issued in Opposition against European Patent Application No. 03 744 867.7, dated Nov. 10, 2014, (12 pages) and Minutes of the Oral Proceedings held Sep. 18, 2014, (25 pages).

* cited by examiner

*Primary Examiner* — Hasan Ahmed
(74) *Attorney, Agent, or Firm* — Fitzpatrick, Cella, Harper & Scinto

(57) ABSTRACT

The present invention relates to a process for the preparation of an intravaginal matrix drug delivery device. The process comprises the steps of combining at least one therapeutic agent in a therapeutically effective amount with at least one biocompatible elastomeric polymer to form a mix; curing said mix in a mold having a shape of said intravaginal drug delivery device, to form a polymer matrix; and maturing said polymer matrix to form the intravaginal drug delivery device.
The maturing step alters the release rate characteristics of a device prepared in accordance with the process of the invention.

9 Claims, No Drawings

INTRAVAGINAL MATRIX DRUG DELIVERY DEVICES

BACKGROUND OF THE INVENTION

Field of the Invention

This invention relates to intravaginal matrix drug delivery devices. Intravaginal drug delivery devices are designed specifically for intravaginal use and include tablets, pessaries, rod-shapes, ring-shapes and films for adhesion to the mucosal epithelium. Whilst these latter systems can be based on compressed powders, hydrogels, waxes or elastomers, the present invention concerns itself solely with intravaginal matrix drug delivery devices formed from "elastomers", as defined hereinafter.

Intravaginal elastomer drug delivery devices, designed to deliver steroidal sex hormones, are well known in the art. Jackanicz (Jackanicz, T. M., Vaginal Contraception: New Developments. Harper and Row, Hagerstown, pp. 201-212, 1979) teaches that three basic designs of intravaginal elastomer drug delivery device are possible, though additional design variations do exist. The three basic types are the homogeneous design, the shell design and the core design, but the present invention concerns itself solely with the homogeneous or "matrix" design:— a) The homogeneous or "matrix" design, in which the active (therapeutic) agent (or drug) is homogeneously distributed in an elastomeric system. This design provides for an exponential (first order) release decay, characterised by an initially high release of drug on day 1, known as a "burst" effect, followed by a lower maintenance release rate of drug on day 2 and on subsequent days. It is accepted that this design cannot sustain a controlled, substantially constant drug release rate, which will be recognised by those skilled in the art as "zero order release", over a prolonged period.

b) The shell design, in which the active (therapeutic) agent is contained in a narrow band (or annulus) between a non-medicated central elastomeric core and a narrow, outer rate controlling non-medicated elastomeric sheath.

c) The core design, in which the active (therapeutic) agent is homogeneously mixed with an elastomeric polymer to form a homogeneous core, the whole being surrounded by a rate controlling, non-medicated elastomeric sheath.

It is an object of the present invention to provide an intravaginal matrix drug delivery device whose day 1 "burst" effect is adjusted as desired.

It is an object of a preferred embodiment of the present invention to provide an intravaginal matrix drug delivery device whose release rate characteristics are substantially independent of shelf life.

It is a further object of a preferred embodiment of the present invention to enable a therapeutic (active) agent loading, hereinafter referred to as a drug loading, of greater than 5% (w/w) with respect to the total weight of the polymer matrix.

Accordingly, the present invention provides, in a first aspect, a process for the preparation of an intravaginal matrix drug delivery device and, in a second aspect, an intravaginal matrix drug delivery device so prepared.

SUMMARY OF THE INVENTION

This invention is directed to a process for the preparation of an intravaginal matrix drug delivery device, the process comprising the steps of:

combining at least one therapeutic agent in a therapeutically effective amount with at least one biocompatible elastomeric polymer to form a mix;

curing said mix in a mould having a shape of said intravaginal drug delivery device, to form a polymer matrix; and maturing the polymer matrix to form the intravaginal drug delivery device.

The selection of a drug loading range, together with the maturing step of the process of the present invention, enables tailoring of the day 1 "burst" effect as desired.

The maturing step of the process of the present invention also enables a device whose release rate characteristics are substantially independent of shelf life. By "substantially independent of shelf life" is meant a release profile which is substantially constant during storage up to the assigned expiry date, i.e., over the assigned storage period.

There is no teaching in the scientific or patent literature as to how altering a drug loading in the range of 5% to 60% (w/w), for drugs of varying solubility in the polymer matrix itself, affects the release rate characteristics of a matrix device, despite the advantages that might ensue from knowing how to modify release profiles from such a device. Specifically, increasing the drug loading above 30% (w/w), with respect to the total weight of the polymer matrix and subjecting the polymer matrix to maturing, reduces day 1 release rates following insertion of the device into the vaginal space of a user, from a device of matrix design. This effect is more marked with increasing solubility of the drug in the polymer matrix. Without wishing to be bound by theory, it is believed that the drug loading affects the rate of curing. This has the effect of tightening the otherwise loose structure of the cured polymer matrix.

Alternatively, reducing the drug loading below 30% (w/w) and subjecting the polymer matrix to maturing, increases day 1 release rates following insertion of the device into the vaginal space of a user, from a device of matrix design. This effect is more marked with reducing solubility of the drug in the polymer matrix. Without wishing to be bound by theory, it is believed that the maturing step, by raising the temperature and time, forces the drug towards the surface of the device.

Advantageously, the curing step is carried out under temperature and time conditions sufficient to produce a polymer matrix that is shape-retaining, i.e., can be removed from a mould. If the elastomer is silicone, and this is preferred, the curing step should be carried out at either 50-100° C., preferably at 60-90° C., for 1-10 minutes, preferably for 1.5 to 4 minutes, or, alternatively, at room temperature (15-25° C.) for 1-24 hours.

Advantageously, the maturing step is carried out under temperature and time conditions sufficient to alter the release rate characteristics of the device. Specifically, the maturing step can adjust at least the "burst" effect on day 1, depending on, primarily, the drug loading (% w/w) in the device and, secondarily, on the solubility of the drug in the polymer matrix itself.

The maturing step can also adjust at least the rate of drug release, post-day 1 (referred to hereinafter as the "maintenance" release rate), depending on the drug loading (% w/w) in the device. More specifically, if the drug loading is less than 30% (w/w), a marked increase in the "burst" effect on day 1 is observed together with a subsequent maintenance release (i.e., release on day 2 and subsequent days) increase. If the drug loading is greater than 30% (w/w), a decrease in the "burst" effect on day 1 is observed, this effect being more marked with increasing solubility of the drug in the polymer matrix.

If the elastomer is silicone, the maturing step can be carried out at 40-100° C., preferably 50-80° C., for 2 to 72 hours, preferably 12-30 hours, more preferably 16-24 hours.

Optionally, the process of the invention includes the further step of aging the matured polymer matrix. The aging step can be carried out at 15-30° C., optionally at room temperature (15-25° C.), for 5-40 days.

The maturing step or the maturing and aging steps serve, unexpectedly, to produce a device whose release characteristics are substantially independent of shelf life.

Before the maturing or the maturing and aging steps, the polymer matrix may, if desired, be housed in an individual pouch.

A second aspect of the invention is directed to an intravaginal drug delivery device whenever prepared by the process of the first aspect of the present invention. Such a device of the present invention provides a means of intravaginal drug delivery in a convenient and high compliance manner with a preferred dosing strategy. Specifically, a drug loading in the range 30% to 60% (w/w), with respect to the total weight of the polymer matrix, enables a decreased day 1 release rate following insertion into the vaginal space of a user, from a device of matrix design, whilst a drug loading in the range 5% to 30% (w/w), with respect to the total weight of the polymer matrix, enables an increased day 1 release rate, together with an increased release, post day 1, i.e., an increased maintenance release rate.

Whilst specific temperature and time conditions have been disclosed for the maturing and aging steps for a silicone elastomer, the present invention is by no means limited thereto. It is within the ordinary skill of the skilled man to determine appropriate conditions for the maturing and aging steps, for any elastomer disclosed hereinafter.

Advantageously, the amount of therapeutic agent(s) included in the polymer matrix is/are selected to provide the desired therapeutic agent(s) release characteristics.

More advantageously, the mix of the at least one therapeutic agent with the at least one biocompatible elastomeric polymer includes a crosslinking agent and, optionally, a catalyst.

Even more advantageously, the mix of the at least one therapeutic agent with the at least one biocompatible elastomeric polymer includes a release enhancing excipient and, optionally, a crosslinking agent and, further optionally, a catalyst.

The invention further provides a method for increasing day 1 release of at least one therapeutic agent from an intravaginal matrix drug delivery device during the first day following insertion of the device into the vaginal space of a user, the method comprising preparing a device in which less than 30% (w/w) of the at least one therapeutic agent is used to form the mix and, preferably, the at least one therapeutic agent has a solubility in silicone oil at 25° C. of less than 0.1 mg/ml; and inserting the device in the vaginal space of the user. The invention also provides use of less than 30% (w/w) of the at least one therapeutic agent in the mix and, preferably, use of at least one therapeutic agent having a solubility in silicone oil at 25° C. of less than 0.1 mg/ml, to increase day 1 release of the at least one therapeutic agent from an intravaginal matrix drug delivery device.

The invention further provides a method for decreasing release of at least one therapeutic agent from an intravaginal matrix drug delivery device during the first day following insertion of the device into the vaginal space of a user, the method comprising preparing a device in which greater than or equal to 30% (w/w) of the at least one therapeutic agent is used to form the mix and, preferably, the at least one therapeutic agent has a solubility in silicone oil at 25° C. of greater than or equal to 0.1 mg/ml; and inserting the device in the vaginal space of the user. The invention also provides use of greater than or equal to 30% (w/w) of the at least one therapeutic agent in the mix and, preferably, use of at least one therapeutic agent having a solubility in silicone oil at 25° C. of greater than or equal to 0.1 mg/ml, to decrease day 1 release of the at least one therapeutic agent from an intravaginal matrix drug delivery device.

DETAILED DESCRIPTION OF THE INVENTION

The present invention primarily concerns itself with intravaginal delivery of at least one therapeutic agent into the vaginal space of a user.

The term "therapeutic agent" is intended to embrace any agent used in the prophylaxis or therapy of any condition affecting the health of the human or animal species.

The at least one therapeutic agent is generally present in the device of this invention in an amount from about 5 to about 60 w/w % preferably from about 7.5 to about 50 w/w %, and most preferably about 10 to about 40 w/w %, by weight of the polymer matrix. However, the amount of therapeutic agent may clearly be varied depending on, for example, the desired dosing level, the particular therapeutic agent, the release rate effect of excipients used in the device, and the particular elastomeric system employed.

The term "elastomer" is intended to mean an amorphous high polymer (or mixture thereof) above its/their glass transition temperature. Elastomers can be stretched and retracted rapidly; exhibit high strength and modulus when stretched; and recover fully when the stress is removed. The term "elastomer" includes covalently-linked elastomers, in which the polymer(s) is/are permanently crosslinked to restrain gross mobility, and thermoplastic elastomers, in which the polymer(s) is/are reversibly crosslinked to restrain gross mobility.

Examples of suitable biocompatible elastomers include, but are not limited to, silicones (organo polysiloxanes including dimethylpolysiloxanes), polyethylene-co-poly (vinyl acetate), styrene-butadiene-styrene block copolymers, polyphosphazenes, poly(isoprene), poly (isobutylene), polybutadienes, polyurethanes, nitrile rubbers, neoprene rubbers or mixtures thereof. Silicones are particularly preferred.

Preferred elastomers include hydroxyl-terminated organopolysiloxanes (such as polydimethylsiloxanes) of the RTV (room temperature vulcanising) type, which harden to elastomers at room temperature or higher, following the addition of cross-linking agents in the presence of curing catalysts. Suitable cross-linking agents and curing catalysts are well known in the art. A typical curing catalyst would be stannous octoate. Curing temperatures and times will vary, depending on the particular elastomer(s) used. For example, the curing temperature may vary between room temperature (15-25° C.) and 150° C. but is preferably within the range 50-100° C., optionally 60-90° C. The curing time may vary between a few seconds and up to 24 hours, depending on the elastomer(s) used and the curing temperature chosen.

Other suitable elastomers include two-component dimethylpolysiloxane compositions using platinum as the curing catalyst and at a curing temperature of from room temperature to an elevated temperature.

Intravaginal elastomer drug delivery devices of the present invention may have any shape and be of any dimensions compatible with intravaginal administration to the human female or other animal. With the requirements imposed by drug delivery kinetics, a particularly preferred intravaginal drug delivery device according to the present invention is a ring. Such a ring can be self-inserted high into the vagina, where it is held in place due to its shape and inherent elasticity. More preferred is a drug delivery device in the form of a ring, in which the elastomer is silicone.

Advantageously, the intravaginal drug delivery device may contain one or more other pharmaceutically compatible agents. Such agents include other therapeutic (pharmacologically active) agents, as well as, pharmacologically inactive agents known in the art as pharmaceutical excipients. By "pharmaceutically compatible, pharmacologically inactive" agent, is meant any agent not intended for use in the prophylaxis or therapy of any condition affecting the health of the human or animal species. Examples of other therapeutic (pharmacologically active) agents that may be advantageous include, but are not limited to, a local anaesthetic such as lidocaine or a local analgesic or a mixture thereof. Examples of pharmacologically inactive agents that may be advantageous include, but are not limited to, hydrophilic compounds that enhance the rate of release of the at least one therapeutic agent from the device, for example, polymers such as povidone or polyvinylpyrrolidone (PVP); modified cellulose ethers, such as hydroxyethylcellulose, hydroxypropylcellulose and hydroxypropylmethyl-cellulose; microcrystalline cellulose, polyacrylic acid, carbomers, alginic acid, carrageenan, cyclodextrins, dextrin, guar gum, gelatin, xanthan gum, lactose, isopropyl myristate and other fatty acid esters; and agents such as sugars. When employed, the release rate enhancing excipient is generally present in an amount of about 0.5 to about 40 w/w %, preferably about 2.5 to about 20 w/w % and more preferably about 2.5 to about 15 w/w %, by weight of the polymer matrix.

The effect of maturing step or, alternatively, the maturing and aging steps on release rate profile is dependent on physico-chemical drug properties i.e. solubility in the polymer matrix itself; and drug concentration (loading).

For example, for a relatively low drug loading of less than 30% (w/w), for example, about 10 or 20% w/w, maturing, or maturing and aging, of a matrix device comprising at least one therapeutic agent, not being of "high" solubility, will increase the magnitude of Day 1 release. This effect is more pronounced for a drug of higher solubility, not being of "high" solubility as defined below, in the polymer matrix.

For a relatively high drug loading of greater than 30% (w/w) (e.g., about 35-40% w/w), maturing or maturing and aging will decrease the magnitude of Day 1 release. This effect is more pronounced for a drug of lower solubility in the polymer matrix.

By "relatively low" drug loading, is meant a drug loading of less than 30% (w/w), optionally less than 25% (w/w) or even less than about 20% (w/w), perhaps in the range of 10-20% (w/w), all by total weight of the mix.

By "relatively high" drug loading, is meant a drug loading of greater than 30% (w/w), optionally greater than about 35% (w/w), perhaps in the range of 35-40% (w/w), all by total weight of the mix.

For a drug of high solubility in the polymer matrix, at a drug loading of 30% (w/w) or less, maturing, or maturing and aging, will have no observable effect on day 1 release. By "high solubility" where the polymer matrix is silicone, is meant a solubility in liquid silicone at 25° C. of 0.24 mg/ml or greater. The skilled man will appreciate that, if the polymer matrix is changed, the definition of "high solubility" would need to be assessed in that particular polymer matrix.

By "higher solubility" is meant, a solubility in silicone oil at 25° C. of greater than 0.1 mg/ml, but less than 0.24 mg/ml. Thus, the solubilities of testosterone and terconazole in silicone oil at 25° C. are 0.14 mg/ml and 0.20 mg/ml, respectively.

By "low solubility" is meant a solubility in silicone oil at 25° C. of less than 0.1 mg/ml. Thus, the solubility of metronidazole and acyclovir are 0.006 mg/ml and <0.08 mg/ml, respectively, in silicone oil at 25° C.

Although a matrix device usually shows first order release decay, the "maintenance" rate of drug release, following the initial 24 hour period, can be adapted to "appear" substantially linear if the diffusional distance that the drug must travel from the receding drug boundary to the outer surface of the device is as small as possible. This, in effect, means that a drug loading of less than 30% (w/w) can be employed, together with the above-mentioned maturing conditions, to encourage migration of the drug towards the periphery of the device. This enhanced migration effect is more pronounced for drugs of low solubility. Alternatively, a drug loading of greater than 30% can be employed, together with the maturing conditions, to tighten the structure of the device. This, in turn, inhibits migration of the drug towards the periphery of the device, an effect which is more pronounced for drugs of higher solubility.

The geometry of the ring (where the device is a ring) also plays a role in achieving the desired drug release characteristics—in the present context, the term "geometric" encompasses the overall diameter of the ring and its cross-sectional diameter.

The particle size of the at least one therapeutic agent may be varied to alter the release rate characteristics of the device of this invention, in the form of a matrix design device.

Several embodiments of the invention will now be described by reference to the following examples. It should be understood that these embodiments are disclosed solely by way of further illustrating the invention and should not be taken in any way to limit the scope of said invention.

General Method of Manufacture

An intravaginal drug delivery device according to the present invention can be prepared by blending 94.24 parts by weight of a hydrophobic elastomeric polymer (polydimethylsiloxane) containing about 10% w/w diatomaceous earth as the filler, with 5.76 parts by weight of a cross-linking agent, n-propylorthosilicate, to form an elastomer mix. One suitable hydrophobic elastomeric polymer is stannous octoate-cured polydimethylsiloxane polymer, a suitable example of which is Dow Corning 382. The appropriate amount of the at least one therapeutic agent was then added, to form a mix. Optionally, additional pharmacologically active agents or pharmaceutical excipients can be included at this stage by similarly blending them into the mix—thus, the rings of Examples 2 and 5 each contain 10% (w/w) of a pharmaceutical excipient, namely, isopropyl myristate and lactose, respectively. Prior to injection moulding or extrusion, the drug-containing mix was activated by blending 140 parts by weight of this mix with 1 part by weight of a catalyst, for example, stannous octoate. The resultant final active mix is injected into a suitable mould and cured. The mould is then opened, following which the device is removed and trimmed.

The geometric characteristics of the device can be varied as required by the use of appropriately sized moulds or extrusion nozzles, as will be obvious to those skilled in the art.

Example 1—Metronidazole

The metronidazole used had a particle size distribution in which 90% is less than 90 µm and 50% is less than 20 µm. The appropriate amount of metronidazole, which was added to the aforementioned elastomer mix, was 40% (w/w), by weight of the final manufactured device. This active mix is injected into a suitable mould (cross-sectional diameter=9.5 mm, outer diameter=56 mm) and cured at 90° C. for 4 minutes. The resultant matrix intravaginal drug delivery device has a ring geometry of 9.2 mm (cross-sectional diameter) and 54 mm (outer diameter). The ring is subjected to a maturing step at 60° C. for 16 hours, followed by, optionally, an aging step in an individual pouch, specifically, subsequent storage at ambient temperature (15-25° C.), to improve the mechanical and release characteristics.

In Vitro Drug Release: Example 1

These release rates were determined in 0.9% (w/v) saline. Each ring was suspended in saline, in a volume of 500 ml for day 1 and in 250 ml for each of the subsequent days. The flasks were maintained at 37° C. in a shaking incubator, the saline being refreshed every 24 hours.

Typical in vitro release rates are shown below, both for a control ring with no maturing or aging step (n=6); for a ring of the present invention with maturing at 60° C. for 16 hours (n=12); and for a ring (n=3) of the present invention with maturing at 60° C. for 16 hours followed by aging (storage, in individual pouches, at a controlled temperature of 25° C. and at 60% relative humidity) for 3 weeks:

| Day | No maturing or aging | Matured at 60° C./16 hrs | Matured at 60° C./16 hrs and aged (stored at the controlled temperature for 3 weeks) |
|---|---|---|---|
| | Mean (% R.S.D.) Drug release rate (mg/day) | | |
| 1 | 82.9 (4.0) | 74.4 (3.4) | 70.5 (0.4) |
| 2 | 42.0 (2.3) | 42.3 (3.8) | 48.6 (2.3) |
| 3 | 31.5 (3.2) | 33.6 (3.9) | 37.2 (1.6) |
| 4 | 24.2 (2.9) | 28.5 (3.9) | 33.1 (3.6) |
| 5 | 21.2 (5.7) | 24.4 (3.3) | 30.1 (1.7) |
| Mean of 2-5 | 29.7 | 32.2 | 37.3 |

These data suggest that the maturing step and the optional aging step serve to alter the release rate characteristics of the intravaginal drug delivery device. Specifically, the release rate on day 1, or "burst" effect, is reduced to 89.7% and 85.0%, respectively (relative to the control), whilst the maintenance release rate (mean of days 2-5), post-day 1, is increased to 108.4% and 125.6%, respectively (again relative to the control).

Example 2—Terconazole

The terconazole used had a particle size distribution of which 100% is less than 10 µm. The appropriate amount of terconazole, which was added to the aforementioned elastomer mix, was 37% (w/w), by weight of the final manufactured device. This active mix is injected into a suitable mould (cross-sectional diameter=9.5 mm, outer diameter=56 mm) and cured at 60° C. for 1.5 minutes. The resultant matrix intravaginal drug delivery device has a ring geometry of 9.2 mm (cross-sectional diameter) and 54 mm (outer diameter). The ring is subjected to a maturing step at 50° C. or 60° C. for 24 hours.

In Vitro Drug Release: Example 2

These release rates were determined in 0.9% (w/v) saline. Each ring was suspended in saline, in a volume of 2000 ml for day 1 and in 1000 ml for each of the subsequent days. The flasks were maintained at 37° C. in a shaking incubator, the saline being refreshed every 24 hours.

Typical in vitro release rates are shown below, both for a control ring with no maturing step (n=3); for a ring of the present invention with maturing at 50° C. for 24 hours (n=3); and for a ring (n=3) of the present invention with maturing at 60° C. for 24 hours—all rings were tested within one hour of completion of the maturing step:

| Day | No maturing | Matured at 50° C./24 hrs | Matured at 60° C./24 hrs) |
|---|---|---|---|
| | Mean (% R.S.D.) Drug release rate (mg/day) | | |
| 1 | 94.6 (1.6) | 46.6 (2.5) | 47.0 (3.5) |
| 2 | 23.1 (4.3) | 19.7 (6.2) | 18.9 (2.7) |
| 3 | 14.4 (10.3) | 14.5 (2.4) | 14.4 (4.6) |
| 4 | 12.3 (3.7) | 11.4 (1.5) | 11.5 (2.6) |
| 5 | 14.9 (2.1) | 12.5 (2.5) | 12.1 (2.2) |
| Mean of 2-5 | 16.2 | 14.5 | 14.2 |

These data suggest that the maturing step serves to alter the release rate characteristics of the intravaginal drug delivery device. Specifically, the release rate on day 1, or "burst" effect, is reduced to 49.3% and 49.7%, respectively (relative to the control), whilst the maintenance release rate (mean of days 2-5), post-day 1, is slightly decreased to 89.5% and 87.7%, respectively (again relative to the control). In addition, there is no statistical difference between maturing at 50° C. and at 60° C., each for 24 hours.

Example 3—Testosterone

The testosterone used had a particle size distribution of 100% less than 15 µm. The appropriate amount of testosterone, which was added to the aforementioned elastomer mix, was 10% (w/w), by weight of the final manufactured device. This active mix is injected into a suitable mould (cross-sectional diameter=9.5 mm, outer diameter=56 mm) and cured at 80° C. for 2 minutes. The resultant matrix intravaginal drug delivery device has a ring geometry of 9.2 mm (cross-sectional diameter) and 54 mm (outer diameter). The ring is subjected to a maturing step at 50° C. or 80° C. for 24 hours.

In Vitro Drug Release: Example 3

These release rates were determined in 0.3% (w/v) sodium lauryl sulphate (SLS). Each ring was suspended in SLS, in a volume of 2500 ml for day 1 and in 1000 ml for each of the subsequent days. The flasks were maintained at 37° C. in a shaking incubator, the medium being refreshed every 24 hours.

Typical in vitro release rates are shown below, both for a control ring with no maturing step (n=3); for a ring of the present invention with maturing at 50° C. for 24 hours (n=3); and for a ring (n=3) of the present invention with maturing at 80° C. for 24 hours—all rings were tested one hour of completion of the maturing step:

| Day | No maturing | Matured at 50° C./24 hrs | Matured at 80° C./24 hrs |
|---|---|---|---|
| | | Mean (% R.S.D.) Drug release rate (mg/day) | |
| 1 | 39.6 (0.9) | 44.3 (0.4) | 43.8 (0.4) |
| 2 | 17.5 (0.4) | 22.3 (1.0) | 21.7 (0.5) |
| 3 | 12.5 (1.3) | 16.9 (0.4) | 16.5 (1.8) |
| 4 | 10.2 (1.6) | 14.0 (0.2) | 13.7 (0.8) |
| 5 | 8.7 (1.1) | 12.1 (0.6) | 11.8 (1.0) |
| Mean of 2-5 | 12.2 | 16.3 | 15.9 |

These data suggest that the maturing step alters the release rate characteristics of the intravaginal drug delivery device. Specifically, the release rate on day 1, or "burst" effect, is increased by 111.9% and 110.6%, respectively (relative to the control), whilst the maintenance release rate (mean of days 2-5), post-day 1, is slightly increased to 133.6% and 130.3%, respectively (again relative to the control). In addition, there is no statistical difference between maturing at 50° C. and at 80° C., each for 24 hours on either day 1 release, or maintenance release.

Example 4—Estradiol-3-Acetate

The estradiol-3-acetate used had a particle size distribution of 99% less than 16 µm. The appropriate amount of estradiol-3-acetate, which was added to the aforementioned elastomer mix, was 10% (w/w), by weight of the final manufactured device. This active mix is injected into a suitable mould (cross-sectional diameter=9.5 mm, outer diameter=56 mm) and cured at 80° C. for 2 minutes. The resultant matrix intravaginal drug delivery device has a ring geometry of 9.2 mm (cross-sectional diameter) and 54 mm (outer diameter). The ring is subjected to a maturing step at 50° C. or 80° C. for 24 hours.

In Vitro Drug Release: Example 4

These release rates were determined in 0.3% (w/v) SLS. Each ring was suspended in SLS, in a volume of 2000 ml for day 1 and in 1000 ml for each of the subsequent days. The flasks were maintained at 37° C. in a shaking incubator, the medium being refreshed every 24 hours.

Typical in vitro release rates are shown below, both for a control ring with no maturing step (n=3); for a ring of the present invention with maturing at 50° C. for 24 hours (n=3); and for a ring (n=3) of the present invention with maturing at 80° C. for 24 hours—all rings were tested one hour of completion of the maturing step:

| Day | No maturing | Matured at 50° C./24 hrs | Matured at 80° C./24 hrs |
|---|---|---|---|
| | | Mean (% R.S.D.) Drug release rate (mg/day) | |
| 1 | 45 (3.7) | 42 (2.6) | 39.4 (0.6) |
| 2 | 19.3 (4.7) | 20.0 (1.0) | 19.3 (1.2) |

These data suggest that, for a drug of high solubility, and a relatively low drug loading, there is no significant alteration in day 1 release rate.

Example 5—Acyclovir

The acyclovir used had a particle size distribution of which 100% is less than 24 µm. The appropriate amount of acyclovir, which was added to the aforementioned elastomer mix, was 20% (w/w), by weight of the final manufactured device. This active mix is injected into a suitable mould (cross-sectional diameter=9.5 mm, outer diameter=56 mm) and cured at 60° C. for 1.5 minutes. The resultant matrix intravaginal drug delivery device has a ring geometry of 9.2 mm (cross-sectional diameter) and 54 mm (outer diameter). The ring is subjected to a maturing step at 50° C. or 60° C. for 24 hours.

In Vitro Drug Release: Example 5

These release rates were determined in 0.9% (w/v) saline. Each ring was suspended in saline, in a volume of 2000 ml for day 1 and in 1000 ml for each of the subsequent days. The flasks were maintained at 37° C. in a shaking incubator, the saline being refreshed every 24 hours.

Typical in vitro release rates are shown below, both for a control ring with no maturing step (n=3); for a ring of the present invention with maturing at 50° C. for hours (n=3); and for a ring (n=3) of the present invention with maturing at 60° C. for 24 hours—all rings were tested within one hour of completion of the maturing step:

| Day | No maturing | Matured at 50° C./24 hrs | Matured at 60° C./24 hrs) |
|---|---|---|---|
| | | Mean (% R.S.D.) Drug release rate (µg/day) | |
| 1 | 2595.2 (8.9) | 5660.3 (4.2) | 5775.4 (9.9) |
| 2 | 573.5 (2.8) | 1189.7 (15.0) | 1395.8 (19.0) |
| 3 | 361.9 (3.2) | 786.5 (18.1) | 947.5 (17.2) |
| 4 | 285.3 (11.4) | | |
| 5 | 283.6 (2.8) | | |
| Mean of 2-3 | 467.7 | 988.1 | 1171.7 |

These data suggest that the maturing step alters the release rate characteristics of the intravaginal drug delivery device. Specifically, the release rate on day 1, or "burst" effect, is increased to 218.1% and 222.5%, respectively (relative to the control), whilst the maintenance release rate (mean of days 2 and 3), post-day 1, is also increased to 211.3% and 250.5%, respectively (again relative to the control). There is, therefore, a further difference between maturing at 50° C. and at 60° C., each for 24 hours.

The invention claimed is:

1. A process for increasing the magnitude of the amount of at least one therapeutic agent released from an intravaginal matrix drug delivery device within the first 24 hours of use of an exponential (first order) release decay, the process consisting essentially of preparing an intravaginal matrix drug delivery device by the steps of:
   combining 5% to less than 30% (w/w) of at least one therapeutic agent with at least one biocompatible silicone elastomeric polymer, to form a mix suitable for forming a shape-retaining polymer matrix, in which the at least one therapeutic agent has a solubility in silicone oil at 25° C. of less than 0.1 mg/ml;
   curing said mix at 50-100° C. for 1-10 minutes or at 15-25° C. for 1-24 hours to form the shape-retaining polymer matrix; and
   maturing said shape-retaining polymer matrix under temperature and time conditions sufficient to form the intravaginal drug delivery device to produce a device having altered release rate characteristics, in which said maturing step is carried out at 40-100° C. for 2-72 hours; wherein the magnitude of the amount of said at least one therapeutic agent released from said intravaginal matrix drug delivery device within the first 24 hours of use of an exponential (first order) release decay is increased compared to said shape-retaining polymer matrix that did not undergo the step of maturing.

2. A process according to claim 1, in which said maturing step is carried out at 50-80° C. for 16-24 hours.

3. A process according to claim 1, in which the maturing step is carried out under temperature and time conditions sufficient to produce a device whose release characteristics are substantially independent of shelf life.

4. A process according to claim 1, in which the process additionally comprises a step of aging the matured polymer matrix.

5. A process according to claim 4, in which the aging step is carried out at 15-30° C. for 5-40 days.

6. A process according to claim 4, in which the maturing step and the aging step are carried out under temperature and time conditions sufficient to produce a device whose release characteristics are substantially independent of shelf life.

7. A process according to claim 1, in which the at least one therapeutic agent is in a range of about 10 to about 20% (w/w).

8. A process according to claim 1, wherein the increase in the magnitude of the amount of said at least one therapeutic agent released in the first 24 hours of use of the intravaginal drug delivery device is between 110.6% to 222.5%.

9. A process according to claim 2, wherein the increase in the magnitude of the amount of said at least one therapeutic agent released in the first 24 hours of use of the intravaginal drug delivery device is between 110.6% to 222.5%.

* * * * *